(12) United States Patent
Grodzki et al.

(10) Patent No.: US 12,161,456 B2
(45) Date of Patent: Dec. 10, 2024

(54) MAGNETIC RESONANCE IMAGING USING A DATABASE OF TIMING PARAMETERS

(71) Applicant: Siemens Healthcare GmbH, Erlangen (DE)

(72) Inventors: David Grodzki, Erlangen (DE); Florian Maier, Buckenhof (DE); Axel Joachim Krafft, Hemhofen (DE); Waqas Majeed, Ellicott, MD (US); Himanshu Bhat, Newton, MA (US)

(73) Assignee: Siemens Healthineers AG, Erlangen (DE)

( * ) Notice: Subject to any disclaimer, the term of this patent is extended or adjusted under 35 U.S.C. 154(b) by 134 days.

(21) Appl. No.: 18/104,396

(22) Filed: Feb. 1, 2023

(65) Prior Publication Data

US 2023/0240552 A1 Aug. 3, 2023

(30) Foreign Application Priority Data

Feb. 2, 2022 (EP) .................... 22154813

(51) Int. Cl.
*A61B 5/055* (2006.01)
*G16H 30/40* (2018.01)

(52) U.S. Cl.
CPC ............ *A61B 5/055* (2013.01); *G16H 30/40* (2018.01)

(58) Field of Classification Search
CPC ................................ A61B 5/055; G16H 30/40
See application file for complete search history.

(56) References Cited

U.S. PATENT DOCUMENTS

| 9,568,578 B2 * | 2/2017 | Senegas ............ G01R 33/543 |
| 2017/0023655 A1 * | 1/2017 | Grodzki ............ G01R 33/3804 |
| 2017/0045594 A1 | 2/2017 | Grodzki et al. |
| 2020/0064426 A1 | 2/2020 | Ersoz |
| 2020/0150208 A1 | 5/2020 | Overall et al. |

FOREIGN PATENT DOCUMENTS

EP 4009066 A1 * 6/2022 ........... G01R 33/385

OTHER PUBLICATIONS

Loecher, Michael et al: "A Gradient Optimization Toolbox for General Purpose Time-Optimal MRI Gradient Waveform Design", Magnetic resonance in medicine, vol. 84, No. 6, Jul. 7, 2020 (Jul. 7, 2020), pp. 3234-3245, XP055935487, US ISSN: 0740-3194, DOI: 10.1002/mrm.28384 Retrieved from the Internet: URL:https://onlinelibrary.wiley.com/doi/full-XML/10.1002/mrm.28384.

* cited by examiner

*Primary Examiner* — Gregory H Curran

(74) *Attorney, Agent, or Firm* — Banner & Witcoff Ltd.

(57) ABSTRACT

Techniques are provided for operating an MR scanner that comprises gradient coils configured to generate a field gradient along coordinate axes of a coil coordinate system. The techniques include receiving limit values concerning the field gradient in the coil coordinate system and an MR scan protocol. Expected orientations of a logical coordinate system are then determined and, for each one, a compliant value for a timing parameter is determined and stored in a database. The MR scanner is controlled to carry out an MR scan, and afterwards the orientation is set to a first orientation. A first value for the timing parameter according to the first orientation is determined based on the data stored in the database, and the MR scanner is controlled to carry out a scan sequence according to the first orientation and the first value.

18 Claims, 1 Drawing Sheet

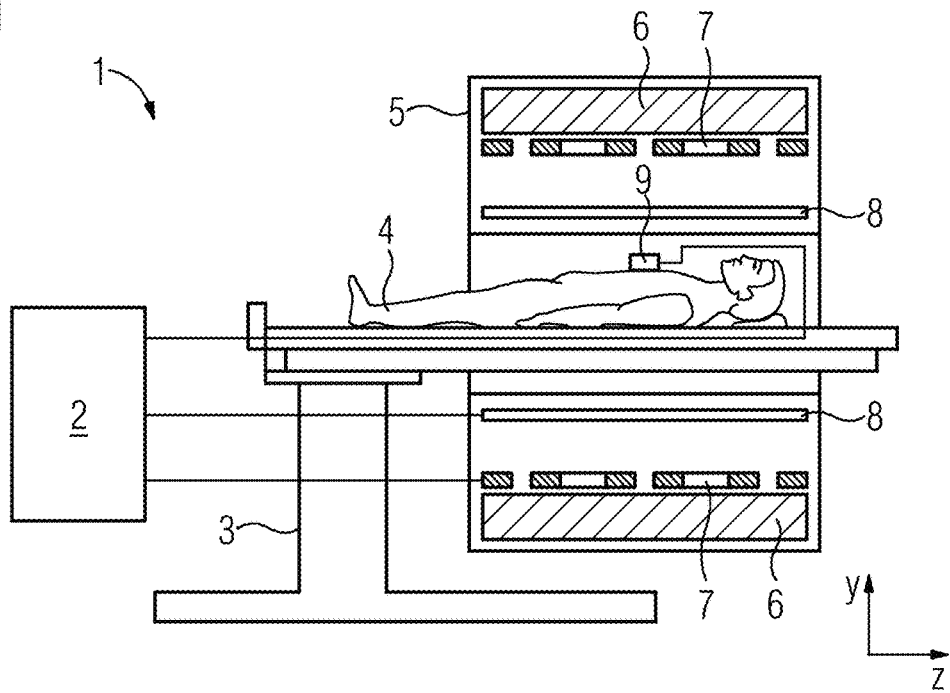
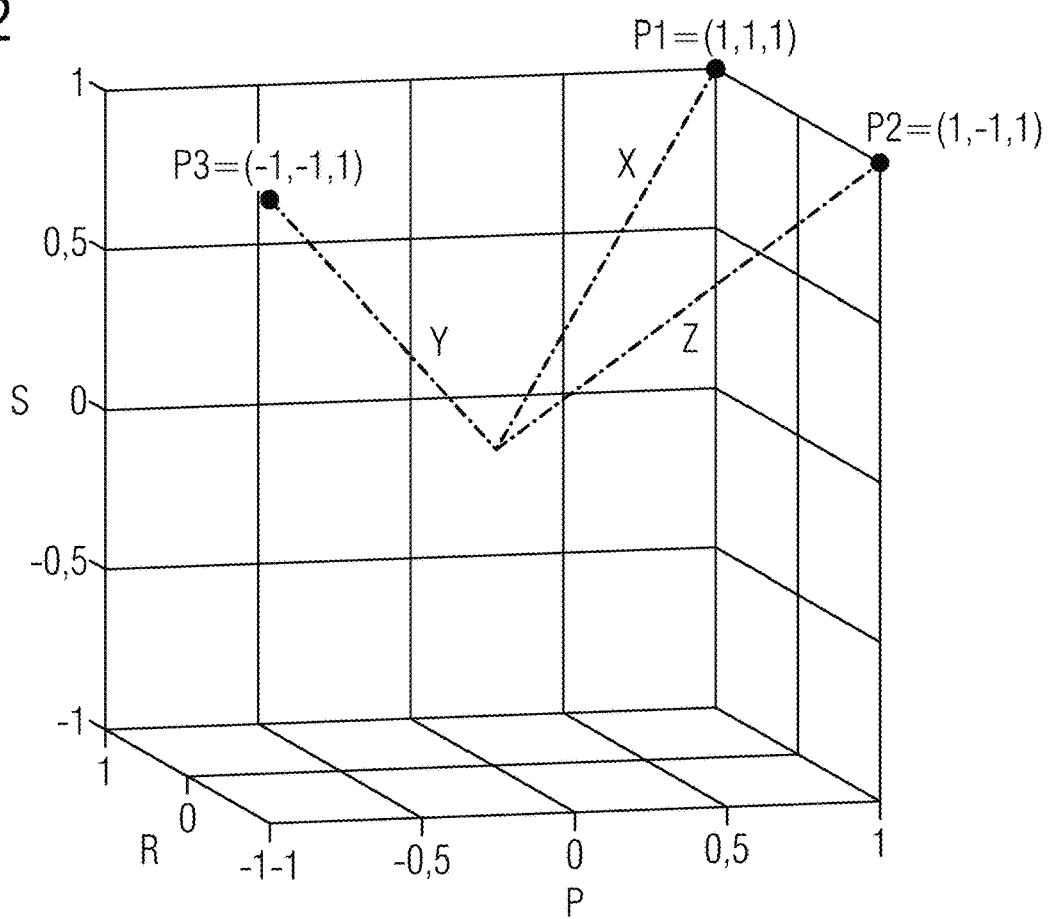

MAGNETIC RESONANCE IMAGING USING A DATABASE OF TIMING PARAMETERS

CROSS-REFERENCE TO RELATED APPLICATIONS

The present application claims priority to and the benefit of Europe patent application no. EP 22154813.4, filed on Feb. 2, 2022, the contents of which are incorporated herein by reference in their entirety.

TECHNICAL FIELD

The present disclosure is directed to a method for operating a magnetic resonance (MR) scanner comprising gradient coils for generating respective components of a magnetic field gradient along respective coordinate axes of a coil coordinate system, wherein predefined gradient limit values concerning the components of the magnetic field gradient in the coil coordinate system are received by a control system, and an MR scan protocol is received by the control system. The disclosure further relates to a corresponding magnetic resonance imaging (MRI) system, and to a computer program product.

BACKGROUND

In magnetic resonance imaging (MRI), an object to be imaged is placed into a strong external magnetic field to align its nuclear spins. An alternating magnetic field is applied to excite the nuclear spins to precess. The precession of the nuclear spins and, in particular, the returning of the nuclear spins from the excited state into a state with lower energy generates an answer signal in the form of an alternating magnetic field, which may be received via respective antennas.

By means of magnetic field gradients, the signals are spatially encoded to allow for a correlation of the received signal to a volume element of the object to be imaged. The received signal is then evaluated to obtain a spatial representation of the object.

In order to achieve a high spatial and temporal resolution while minimizing scan time and off-resonance artifacts, the magnetic field gradients are usually tuned to allow for short MR timing parameters, such as echo time (TE) and repetition time (TR). The magnetic field gradients of an MR sequence are defined in a logical coordinate system, usually denoted as read-axis, phase-axis and slice-axis. The axes of the logical coordinate system do, however, in general not coincide with the physical coordinate axes of the MR scanner, i.e. the axes along which the magnetic field gradients are generated by means of the respective gradient coils. The physical coordinate axes and the physical coordinate system are therefore also denoted as coil coordinate axes and a coil coordinate system, respectively.

On the other hand, physical limitations, for example due to maximum currents that may be applied to the gradient coils, are naturally given according to the coil coordinate system rather than according to the logical coordinate system. Furthermore, the relative orientation of the logical coordinate system with respect to the coil coordinate system, which is also denoted as angulation, is not necessarily fixed but may be adapted during the imaging procedure. In this context, the relevance of a real-time adaptation of the relative orientation is noted.

Depending on the orientation of the logical coordinate system, gradients of different logical axes may overlap on a single coil axis. In this case, the physical constraints of the respective coil axis have to be accounted for. As a consequence, the maximum possible gradient values on the individual coil axes are usually not exploited to avoid an overload in worst case situations regarding the orientation of the logical coordinate system with respect to the coil coordinate system. However, this means that for almost all relative orientations, available power of the gradient system remains unused.

SUMMARY

It is an objective of the present disclosure to achieve a higher degree of utilization of available power for generating magnetic field gradients in magnetic resonance imaging and, in particular, for applications incorporating real-time adaptation of the relative orientation between the coil coordinate system and the logical coordinate system. This objective is achieved by the subject-matter of the embodiments as discussed herein, including that of the claims.

The disclosure is based on the idea of storing compliant values for at least one predefined MR timing parameter for a plurality of expected orientations of a logical coordinate system with respect to a coil coordinate system in a database, and subsequently accessing the database to retrieve respective suitable values for the MR timing parameter when carrying out a scan sequence.

According to an embodiment of the disclosure, a method for operating a MR scanner, e.g. an MR scanner of an MRI system, is provided. The MR scanner comprises gradient coils for generating respective components of a magnetic field gradient along respective coordinate axes of a coil coordinate system. According to the method, predefined gradient limit values concerning the components of the magnetic field gradient in the coil coordinate system are received by a control system, e.g. of the MRI system, which may be for example from a memory device of the MRI system or of the control system. An MR scan protocol is received by the control system, e.g. via a user input interface of the MRI system, based on a corresponding user input or from the memory device.

A plurality of expected orientations of a logical coordinate system with respect to the coil coordinate system are determined, e.g. by the control system. For each of the plurality of expected orientations, at least one respective compliant value for at least one predefined MR timing parameter is determined by the control system depending on the MR scan protocol and depending on the gradient limit values. The at least one compliant value is stored in a database, e.g. a database of the MRI system or the control system, which is for example stored on the memory device. The MR scanner is controlled e.g. by the control system to carry out an MR scan. The orientation of the logical coordinate system with respect to the coil coordinate system is set to a first orientation after the MR scan has been started and e.g. after the at least one compliant value has been stored to the database at least for a fraction of the plurality of expected orientations. At least one first value for the at least one MR timing parameter according to the first orientation is determined based on the database, e.g. by the control system. The MR scanner is controlled, e.g. by the control system, to carry out a scan sequence of the MR scan according to the first orientation and according to the at least one first value for the at least one MR timing parameter and, e.g., according to the scan protocol.

For instance, the at least one compliant value may be stored in the database together with information regarding the respective expected orientation, such that the at least one compliant value is assigned or associated with the respective expected orientation.

The MR scanner may be implemented as a device of the MRI system comprising for example an MR bore, one or more field magnets, the gradient coils, respective RF coils, a receiving and transmitting antennas, etc.

The control system may comprise one or more computing units and/or one or more control units for carrying out the respective steps of the method as described herein. The control units may comprise, for example, drivers and/or other control circuitry to cause the MR scanner to carry out an MR scan. The at least one computing unit may carry out the computational steps involved in the method as described herein, e.g. determining the at least one compliant value for each of the plurality of expected orientations, determining the at least one first value for the at least one MR timing parameter based on the database, and so forth.

However, the at least one computing unit and the at least one control unit are not necessarily strictly separated. In fact, one or more functions or functionalities described herein with respect to the at least one computing unit may be additionally or alternatively be executed by the at least one control unit, or vice versa.

The scan protocol may, for example, be understood as a description or a dataset defining the required parameters for carrying out an MR scan according to individual requirements, according to user settings, etc. For instance, the scan protocol may contain or define a set of scan protocol parameters including parameters defining a field of view, a resolution (e.g. a spatial resolution), an acquisition bandwidth for the MR scan, etc. The scan protocol parameters may also contain parameters defining whether or not specific RF pulses are to be used, for example for achieving saturation effects such as water saturation or fat saturation, whether specific RF pulses for flipping the nuclear spins by certain flip angles should be applied, whether asymmetric echoes are to be allowed, whether (or to which extent) a partial Fourier transform should be carried out, etc. The scan protocol parameters may be for example set individually by a user prior to the start of the MR sequence. Alternatively, pre-stored scan protocols may be provided, for example, on a memory device.

The compliant values for the MR timing parameter may be understood as being compliant with respect to the gradient limit values. For instance, if a corresponding scan sequence is carried out according to the respective orientation, according to the MR scan protocol and according to the at least one compliant value for the at least MR timing parameter, it is ensured that the gradient limit values are not violated or, in other words, the corresponding temporal course of the magnetic field gradient complies with the gradient limit values. That is, none of the gradient limit values is exceeded during the corresponding scan sequence, if the at least one compliant value are used.

In order to determine whether a specific set of values for the MR timing parameters is compliant or not, the control system (e.g. the at least one computing unit), may simulate or estimate the temporal course of the magnetic field gradient according to a known method.

The first orientation may, for example, be set by a user in real-time after the MR scan has been started. For instance, the MR scan may not start with the first orientation but with a different initial orientation. Furthermore, the first orientation may not necessarily follow immediately after the initial orientation, but one or more further orientations may be set after the initial orientation and prior to the first orientation.

For example, in the case of an MRI-assisted interventional procedure, the user may move a device such as a catheter or a camera or another medical device. The orientation and/or position of the device with respect to the coil coordinate system may define the orientation of the logical coordinate system with respect to the coil coordinate system. The current orientation may be obtained from a sensor system that measures the orientation of the device. Alternatively, the orientation may be input by a user using a separate user input device, which may or may not be coupled to the medical device.

For example, to start an MR scan, a user may provide a corresponding instruction to the control system, for example by activating a key, a button, etc. After the instruction has been provided, the control system, e.g. the at least one computing unit, may begin by generating the database and determining and storing the at least one compliant value. The MR scan may be started with a time delay of a few tens or a few hundreds of milliseconds to allow the control system to fill the database with the at least one compliant value at least in part.

The database is thus filled at least partially with respect to the plurality of expected orientations before the first orientation is set. For example, the database may be initialized and the at least compliant value may be determined for all or a fraction of the plurality of expected orientations prior to the start of the MR scan. Alternatively, the database may be generated and/or filled at the beginning of the MR scan after it has been started but at least in part before the first orientation is set. In some implementations, filling the database and determining the at least one compliant value for the plurality of expected orientations may be started prior to the start of the MR scan and continued after the MR scan has been started.

Furthermore, the database may be filled further during the course of the MR scan. It is also possible that after the MR scan has been started, a further plurality of expected orientations are determined, and the corresponding at least one compliant value for the at least one MR timing parameter for the further plurality of expected orientations is determined while the MR scan is being carried out.

The at least one first value for the at least one MR timing parameter is determined in a predefined manner based on the data stored in the database. For example, the computing unit may check the database for the next one of the expected orientations and determine the at least one first value as the at least one compliant value for the next orientation with respect to the first orientation. However, more complex or different approaches are possible and will be explained further below with respect to the various embodiments.

By using a method according to the disclosure, it is achieved that the MR scan, e.g. the scan sequence according to the first orientation, may be carried out to comply with the gradient limit values without overly limiting the MR timing parameters to ensure that, even under worst-case conditions regarding the orientation of the logical coordinate system with respect to the coil coordinate system, the gradient limit values will not be violated. In other words, instead of assuming a worst-case orientation and limiting the MR timing parameters accordingly, the database comprising the at least one compliant value is used. As a fallback, the worst-case situation can still be assumed in case no suitable entry in the database is present.

When the user sets the first orientation during the MR scan and a corresponding first value for the at least one MR timing parameter is determined based on the database, the delay between setting the first orientation and starting of the scan sequence according to the first orientation and the scan protocol is reduced to a minimum, since at this time the at least one first value has already been computed and stored.

Thus, according to the disclosure, a real-time adaption of the orientation is possible without a significant delay in the procedure, since the database has been set up and filled at least partially before the first orientation is set. To this end, different approaches are possible to define the expected orientations, for example based on user inputs or based on empirical values. For instance, since a vast number of different scan protocols are possible in modern MRI systems, it may not be feasible to provide a comprehensive database of orientations and corresponding compliant values for the MR timing parameter for all scan protocols beforehand. According to the disclosure, the database is filled with the at least one compliant value for the different expected orientations after (e.g. only after) the scan protocol is defined, which greatly reduces the overall computational effort and memory requirements.

The coil coordinate system and the logical coordinate system may be defined in, e.g., three-dimensional Cartesian coordinate systems. Consequently, the gradient coils of the MRI system comprise one or more coils for each of the three axes of the coil coordinate system. The axes of the coil coordinate system may be denoted as the X-, Y-, and Z-axis, respectively. Consequently, the gradient coils may be denoted as the X-coils, Y-coils, and Z-coils, with the one or more X-coils being arranged to generate an X-component of the magnetic field gradient along the X-axis, the one or more Y-coils being arranged to generate a respective Y-component of the magnetic field gradient along the Y-axis, and the one or more Z-coils being arranged to generate a Z-component of the magnetic field gradient along the Z-component.

The at least one gradient limit value for the X-, Y-, and Z-axis, respectively, may comprise a limit value for an amplitude of the respective component of the magnetic field gradient and/or a limit value for a slew rate of the respective component of the magnetic field gradient.

The orientation of the logical coordinate system with respect to the coil coordinate system may for example be provided or represented as a rotation matrix, which maps the logical coordinate system to the coil coordinate system, or vice versa. Alternatively, the orientation may be given by an equivalent set of data, such as rotation angles, Euler angles, etc.

The MRI scan may comprise a plurality of scan sequences including the scan sequence carried out according to the first orientation. Each scan sequence may for example be characterized by a corresponding orientation of the logical coordinate system with respect to the coil coordinate system, which may for example be dynamically changed by a user or according to a predefined scheme during the MR scan or, in other words, may be adapted in real-time. During each of the scan sequences, respective MR datasets may be acquired according to standard approaches to generate respective MR images of an object to be imaged.

For instance, carrying out a scan sequence may comprise applying a magnetic field gradient sequence and a corresponding radio-frequency (RF) pulse sequence for exciting or manipulating the nuclear spins of the object to be imaged. To carry out the gradient sequence, the gradient coils may be controlled to generate a respective time-dependent magnetic field gradient.

For example, the MR scan may be carried out accompanying a medical intervention to implement MRI-assisted embodiments of the disclosure. Such applications often use a real-time adaptation of the orientation. However, the embodiments of the disclosure are not limited in this regard, and may be applied to other use cases as well.

According to several implementations of the method, the MR scanner is controlled e.g. by the control system to carry out an MR scan starting with an initial scan sequence of the MR scan according to an initial orientation of the logical coordinate system with respect to the coil coordinate system.

For instance, the orientation may be set to the initial orientation before the orientation is set to the first orientation, and the MR scanner may be controlled to carry out the MR scan starting with the initial orientation.

For the initial orientation, the initial scan sequence may, for example, be carried out according to an initial set of values of the at least one MR timing parameter. To avoid the initial scan sequence violating the gradient limit values, the at least one initial value for the MR timing parameter may be automatically set in a conservative manner, for example, assuming a worst-case orientation.

Alternatively, prior to the initial scan sequence, the control system, e.g. the at least one computing unit, may check whether a temporal course of the magnetic field gradient complies with the gradient limit values for the initial orientation and respective user values of the at least one timing parameter provided by the user. If this is the case, the initial scan sequence may be carried out accordingly; otherwise, the initial scan sequence may be carried out with automatically- or manually-adapted values for the at least one MR timing parameter.

According to several implementations, the plurality of expected orientations is determined as a predefined sequence of orientations, with the sequence starting with the initial orientation. The at least one compliant value for each of the plurality of expected orientations may be determined according to the sequence.

For instance, the sequence of orientations may be a defined order of the involved expected orientations, and the at least one compliant value may be determined one after the other according to the order of the sequence.

Since the sequence starts with the initial orientation, the timing for determining the at least one compliant value may be optimized or tuned such that the probability that, for an orientation which is set later by the user (e.g. the first orientation), the database comprises suitable values to determine the corresponding at least one value for the at least one MR timing parameter, e.g. the at least one first value.

For example, the sequence may be determined such that an orientation angle of the orientation is incrementally changed by a predefined angular increment starting from an initial angle according to the initial orientation.

In general, the orientation of a coordinate system with respect to another coordinate system in three dimensions is fully defined by three rotation angles, for example Euler angles. The orientation angle may be considered as one of the rotation angles. For instance, the sequence of orientations may correspond to different values for one, two, or three of the rotation angles. The individual rotation angles may be incremented according to the sequence in a predefined manner, wherein the initial orientation is defined by three initial orientation angles or three initial rotation angles, respectively.

In alternative implementations, the sequence of orientations may be determined according to a predefined probability distribution concerning the expected orientations.

In other words, empirical information may be provided, which includes information regarding typical courses of the orientation used by the specific user, used for the specific scan protocol, etc. Then, the sequence may be defined such that the respective at least one value for the at least one MR timing parameter is determined first for such orientations, which occur with a higher probability.

In alternative implementations, a user input concerning the expected orientations is received, and the sequence is determined according the user input. For instance, prior to the start of the MR scan, the user may provide via the user input the information, which orientations are going to be used during the MR scan.

According to several implementations, a closest orientation of the plurality of expected orientations with respect to the first orientation is determined, e.g. by the at least one computing unit, and the at least one compliant value of the closest orientation is read from the database to determine the at least one first value.

In other words, the at least one first value corresponds to the at least one compliant value of the closest orientation. Therefore, the number of the plurality of expected orientations may be reduced.

According to several implementations, the at least one first value is determined by interpolating the respective at least one compliant values for two or more of the plurality of expected orientations.

In other words, instead of taking the at least one compliant value of the closest orientation, the at least one compliant values are interpolated, which may on the one hand increase the effectivity of gradient usage, and on the other hand decrease the probability that the gradient limit values are violated.

According to several implementations, it is determined that the first orientation deviates from each of the plurality of expected orientations by more than a predefined tolerance. At least one further compliant value for the at least one MR timing parameter is determined for the first orientation depending on the MR scan protocol, and the gradient limit values and the at least one further compliant value is stored to the database.

For carrying out the scan sequence according to the first orientation, the stored values of the database may nevertheless be used to avoid a delay, for example, depending on the next orientation or based on interpolation. However, additionally the database is augmented by the at least one further compliant value, which may then be used in case the first orientation is set again later during the MR scan or during a further MR scan.

According to several implementations, a further MR scan protocol is received by the control system after the MR scan is finished. It is determined by the control system that the further MR scan protocol matches the MR scan protocol. The MR scanner is controlled to carry out a further MR scan, and the orientation is set to a second orientation after the further MR scan has been started. At least one second value for the at least one MR timing parameter according to the second orientation is determined based on the data stored in the database. The MR scanner is controlled to carry out a further scan sequence of the further MR scan according to the second orientation and according to the at least one second value.

Therein, the second orientation may be identical to or different than the first orientation. For instance, the database, which originally has been generated for the scan protocol, may also be used later in case the same scan protocol is used again for a further MR scan.

According to several implementations, a user input comprising the MR scan protocol is received by the control system, or a further user input is received by the control system, and the MR scan protocol is determined by the control system based on the further user input.

According to several implementations, to determine the at least one compliant value for one of the plurality of expected orientations, at least one initial value for the at least one MR timing parameter is received by the control system, for example, by yet a further user input. A temporal course of the magnetic field gradient during a hypothetical scan sequence according to the respective one of the plurality of expected orientations, e.g. according to the at least one initial value and according to the MR scan protocol, is computed by the control system. The at least one compliant value for the respective one of the plurality of expected orientations is determined as the at least one initial value only if the computed temporal course of the magnetic field gradient complies with the gradient limit values.

In other words, the control system estimates or simulates the temporal course of the magnetic field gradients, and determines whether the gradient limit values are violated. If they are not violated, the at least one initial value may be used as the at least one compliant value; otherwise, the at least one compliant value is different than the at least one initial value.

For instance, if the temporal course of the magnetic field gradient violates the gradient limit values, e.g. one of the gradient limit values, or in other words the temporal course of the magnetic field gradient does not comply with the gradient limit values, the at least one initial value is adapted by the control system. The temporal course of the magnetic field gradient is then re-computed according to the adapted at least one value, e.g. by the control system. The at least one compliant value for the respective one of the plurality of expected orientations is then determined as the adapted at least one value only if the re-computed temporal course of the magnetic field gradient complies with the gradient limit values.

For instance, said steps may be repeated iteratively until the gradient limit values are not violated, and the corresponding at least one value for the at least one MR timing parameter is then used as the at least one compliant value, which is stored in the database.

According to several implementations, to determine the at least one compliant value for one of the plurality of expected orientations, an optimization, e.g. a minimization, of the at least one MR timing parameter, e.g. of all of the at least one MR timing parameters, is carried out by the control system, e.g. by the at least one computing unit. Therein, the MR scan protocol, the respective one of the plurality of expected orientations, and the gradient limit values, are treated as boundary conditions for the optimization. There exist known minimization methods for determining the optimal values for the at least one MR timing parameter based on the corresponding MR scan protocol.

In these implementations, the user does not necessarily have to provide an initial value for the at least one timing parameter, and still an optimal timing may be achieved.

According to several implementations, the at least one MR timing parameter comprises an echo time and/or a repetition time and/or a frame duration, which is an inverse frame rate.

According to a further aspect of the disclosure, an MRI system comprising an MR scanner and a control system is provided. The MR scanner comprises gradient coils for generating respective components of a magnetic field gradient along respective coordinate axes of a coil coordinate system. The control system is configured to receive, e.g. from a memory device of the control system, predefined gradient limit values concerning the components of the magnetic field gradient in the coil coordinate system, and to receive a MR scan protocol. The control system, e.g. at least one computing unit of the control system, is configured to determine a plurality of expected orientations of a logical coordinate system with respect to the coil coordinate system.

The control system, e.g. the at least one computing unit, is configured to determine for each of the plurality of expected orientations, a compliant value for at least one predefined MR timing parameter depending on the MR scan protocol and depending on the gradient limit values. The control system, e.g. the at least one computing unit, is also configured to store the at least one compliant value in a database, for example, a database on the memory device. The control system, e.g. at least one computing unit of the control system, is configured to control the MR scanner to carry out an MR scan. The control system, e.g. the at least one computing unit, is configured to determine that the orientation of the logical coordinate system with respect to the coil coordinate system is set to a first orientation after the MR scan has been started. The control system, e.g. the at least one computing unit, is configured to determine at least one first value for the at least one MR timing parameter according to the first orientation based on the data stored in the database. The control system, e.g. the at least one computing unit, is configured to control the MR scanner to carry out a scan sequence of the MR scan according to the first orientation and the at least one first value.

Further implementations of the MRI system according to the disclosure follow directly from the various embodiments of the method according to the disclosure, and vice versa. For instance, individual features and corresponding explanations relating to the various implementations of the method according to the disclosure apply analogously to corresponding implementations of the MRI system according to the disclosure. For instance, the MRI system according to the disclosure may be designed or programmed to carry out the method according to the disclosure and/or to carry out the method according to the disclosure.

According to a further aspect of the disclosure, a computer program comprising instructions is provided. When the instructions are executed by an MRI system according to the disclosure, e.g. by the control system of the MRI system, e.g. by the at least one computing unit of the control system, the instructions cause the MRI system to carry out a method according to the disclosure.

According to a further aspect of the disclosure, a computer-readable storage medium storing a computer program according to the disclosure is provided.

The computer program, as well as the computer-readable storage medium, may be denoted as respective computer program products comprising the instructions.

If it is mentioned in the present disclosure that a component of the MRI system according to the disclosure, e.g. the control system of the MRI system, is adapted, configured, designed to, etc., perform or realize a certain function, to achieve a certain effect, or to serve a certain purpose, this can be understood such that the component, beyond being usable or suitable for this function, effect, or purpose in principle or theoretically, is physically tangible and capable of executing or realizing the function, achieving the effect, or serving the purpose by a corresponding adaptation, programming, physical design, and so on.

A computing unit may e.g. be understood as a data processing device, which comprises processing circuitry. The computing unit can therefore e.g. process data to perform computing operations. This may also include operations to perform indexed accesses to a data structure, for example a look-up table (LUT).

For instance, the computing unit may include one or more computers, one or more microcontrollers, and/or one or more integrated circuits, for example, one or more application-specific integrated circuits (ASICs), one or more field-programmable gate arrays, (FPGAs), and/or one or more systems on a chip (SoC). The computing unit may also include one or more processors, for example one or more microprocessors, one or more central processing units (CPUs), one or more graphics processing units (GPUs), and/or one or more signal processors, e.g. one or more digital signal processors (DSPs). The computing unit may also include a physical or a virtual cluster of computers or other of said units.

In various embodiments, the computing unit includes one or more hardware and/or software interfaces and/or one or more memory units.

A memory unit may be implemented as any suitable type of memory such as a volatile data memory, for example a dynamic random access memory (DRAM), as a static random access memory (SRAM), as a non-volatile data memory, for example a read-only memory (ROM), a programmable read-only memory (PROM), an erasable read-only memory (EPROM), an electrically erasable read-only memory (EEPROM), a flash memory or flash EEPROM, a ferroelectric random access memory (FRAM), a magnetoresistive random access memory (MRAM) a phase-change random access memory (PCRAM), etc.

BRIEF DESCRIPTION OF THE DRAWINGS

In the following, the disclosure will be explained in detail with reference to specific exemplary implementations and respective schematic drawings. Herein:

FIG. 1 illustrates an exemplary implementation of an MRI system according to the disclosure; and FIG. 2 illustrates an exemplary coil coordinate system and an exemplary logical coordinate system according to the disclosure.

DETAILED DESCRIPTION OF THE DISCLOSURE

FIG. 1 illustrates an exemplary implementation of an MRI system according to the disclosure. The MRI system 1 comprises an MR scanner 5 with a field magnet 6, which may generate a static magnetic field for aligning the nuclear spins of an object 4 to be imaged. The MR scanner 5 may comprise a bore comprising an imaging region, wherein the static magnetic field is extremely homogenous with respect to its magnetic field strength or its absolute value within the imaging region. The object 4 may be arranged on a patient table 3, which may be movable to vary the position of the object 4.

The field magnet 6 may for example comprise a superconducting magnet that is an electromagnet with a superconducting coil. In this way, static magnetic fields up to 3T or above may be achieved. For lower field strengths, permanent magnets or electromagnets with normal conducting coils may also be used.

The MR scanner 5 further comprises gradient coils 7, which may generate respective variable magnetic fields along each of the three spatial dimensions X, Y, and Z, and superpose the variable magnetic fields with the basic magnetic field to achieve a spatial encoding. The gradient coils 7 may be coils comprising "normal" (versus superconducting) conducting wires. For instance, the gradient coils 7 may comprise one or more coils configured to generate a magnetic field gradient in the X-direction, one or more coils configured to generate magnetic field gradients in the Y-direction, and one or more gradient coils configured to generate magnetic field gradients in the Z-direction.

Furthermore, the MR scanner 5 may comprise one or more sending coils 8 configured to generate (i.e. transmit) RF-pulses for exciting nuclear spins to precess in the respective magnetic field. The sending coils 8 may also operate as receiving coils to receive MR signals in response to the nuclear spin excitement and precession resonance. Alternatively or in addition, one or more dedicated receiving coils 9, such as body coils arranged in the immediate environment of the object 4, may be used.

The MRI system 1 further comprises a control system 2, which may contain one or more computing units and one or more control units for controlling the MR scanner 5.

In general, the coil axes X, Y, and Z do not necessarily correspond to the logical axes read R, phase P, and slice S. For example, the respective angulation of the slice to be imaged by means of an MR scan is given by a rotation matrix transforming the logical coordinate system R, P, S into the coil coordinate system X, Y, Z:

R11 R12 R13
R21 R22 R23
R31 R32 R33

FIG. 2 illustrates an exemplary coil coordinate system and an exemplary logical coordinate system according to the disclosure. With reference to FIG. 2, the logical coordinate system is shown with the read-axis R, the phase-axis P, and the slice-axis S, and in addition the coil coordinate system is shown with the coil axes X, Y, Z. Furthermore, three points P1, P2, P3 are shown together with their coordinates in the logical coordinate system R, P, S.

The functionality of the MRI system 1 is described in more detail in the following with respect to an exemplary implementation of a method according to the disclosure.

Predefined gradient limit values concerning the components of the magnetic field gradient in the coil coordinate system X, Y, Z, as well as an MR scan protocol, are received by the control system 2. For instance, the gradient limit values may comprise a limit value for the absolute value of the magnetic field gradients in the coil coordinate system X, Y, Z and, for example, a limit value for the respective slew rates of the magnetic field gradient components in the coil coordinate system X, Y, Z, for example, may be received from the memory device. In alternative implementations, the limit values for the absolute value and/or the slew rates may be different for the different coil axes X, Y, Z.

The MR scan protocol may for example be set up for an interventional scan by a user and may for example comprise a field of view (FOV), a resolution, etc. For example, the MR scan protocol may be chosen according to a balanced steady-state free precession (bSSPF) sequence or a gradient echo (GRE) sequence. The user may also define an initial orientation of the logical coordinate system R, P, S and desired values for MR timing parameters such as echo time (TE) and repetition time (TR). For setting up the MR scan protocol, the maximum absolute values and slew rates possible on the coil axes X, Y, Z according to the gradient limit values may also be allowed for each logical axis R, P, S. This may, however, result in a violation of the gradient limit values on the coil axes X, Y, Z.

Considering FIG. 2, one may assume, for example, that the same slew rates and gradient amplitude are present in all three coordinate axes X, Y, Z. The point P1=(1, 1, 1) in the logical coordinate system R, P, S corresponds to (1, 0, 0) in the coil coordinate system X, Y, Z, the point P1=(1, −1, 1) in R, P, S corresponds to (0, 0, 1) in X, Y, Z and P3=(−1, −1, 1) corresponds to (0, 1, 0) in X, Y, Z. In this worst case situation, the amplitudes and slew rates on the X axis are increased by factor of $(3)^{1/2}$ with respect to the logical coordinate system.

The user may initiate an MR scan. The control system 2 may then check if the selected angulation, i.e. the initial orientation, can be realized without violating the gradient limit values, or if the MR timing parameters need to be adapted. In the latter case, the control system 2 applies a known automated solving algorithm to mitigate the violation, for example by decreasing the allowed logical gradient amplitudes and slew rates and, as a result, "stretching" TE and TR, until the violation is resolved.

The control system 2 initializes a database to store different expected orientations and the compliant MR timing parameters.

Shortly before the MR scan begins and/or during the MR scan, the control system 2 fills the database continuously with additional data-points that are being calculated for a plurality of expected orientations of the logical coordinate system R, P, S. To determine the plurality of expected orientations, the control system 2 may for example start with the initial orientation angles set by the user and incrementally alter them, for example in steps of 5° or 10°, so that different possible orientation ranges are filled into the database.

Alternatively, orientations with a higher probability may be used first for the calculation of the compliant MR timing parameters. Such probabilities may for example be derived from existing imaging data, which may also be also specific for the current application. The probabilities may also be updated continuously using information from every scan that is performed.

While the MR scan is running, the database may continuously be filled further, for example until all possible orientation angles, rounded to some predefined tolerance, for example 1° or 2°, are covered, and respective compliant MR timing parameters are stored to the database.

After the MR scan has been started, the MR scanner 5 is controlled to carry out an initial scan sequence according to the initial orientation. Then, the orientation is changed in real-time, for example by the user. Respective suitable values for the MR timing parameters are determined by the control system 2 based on the data stored in the database, and the control system 2 controls the MR scanner 5 to carry out a scan sequence accordingly. Consequently, no extra calculation time is required, such that the MR scan may continue without any disruption.

It is also possible that after a change of the orientation, the exact possible MR timing parameters for the changed orientation may be calculated, if not already existing, and used in further repetitions Alternatively or in addition, MR timing parameters for an orientation absent in the database can be interpolated from the existing database entries. For example, parameters for an orientation angle of 32° can be interpolated from the parameters for 35° and 30°, assuming a database that is filled with data in accordance with 5° angle increments.

For example, the stored MR timing parameters associated with the closest orientation present in the database can be used as initial values for iterative optimization. A time limit can be set to allow only a certain number of iterations before the parameters are applied for the next image. The result of the additional iterations may be stored in the database.

Orientations that are used more often benefit from higher numbers of iterations for optimization.

Alternatively or in addition, the user may define specific scan plane angulations and respective orientations prior to the start of the real-time sequence, as for example in cardiac exams where certain anatomical orientations are scanned such as short axis, long axis, and four chamber views. The optimized MR timing parameters for these pre-defined orientations may also be included in the database upfront, so that they are immediately available at runtime without the need for interpolation or similar approaches.

It is also possible that after the MR scan, the database including the selected start values is stored at the MR scanner 5 or in a cloud, so that when the same scan protocol is chosen again, the database does not need to be re-calculated.

As described, the disclosure allows for the use of maximum possible gradients (or at least an increase in possible gradients) on each logical axis even in real-time scenarios. To this end, a database that is populated and that contains possible orientations that might be selected at runtime of the real-time application is used.

The various components described herein may be referred to as "units" or systems." Such components may be implemented via any suitable combination of hardware and/or software components as applicable and/or known to achieve the intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer readable medium. Regardless of the particular implementation, such units or systems, as applicable and relevant, may alternatively be referred to herein as "circuitry," "controllers," "processors," or "processing circuitry," or alternatively as noted herein.

What is claimed is:

1. A method for operating a magnetic resonance (MR) scanner comprising gradient coils configured to generate respective components of a magnetic field gradient along respective coordinate axes of a coil coordinate system, the method comprising:
   receiving, via a control system, predefined gradient limit values identified with components of the magnetic field gradients in the coil coordinate system;
   receiving, via the control system, an MR scan protocol;
   determining, via the control system, a plurality of expected orientations of a logical coordinate system with respect to the coil coordinate system;
   for each of the plurality of expected orientations, determining, via the control system, a respective compliant value for a predefined MR timing parameter based upon the MR scan protocol and the predefined gradient limit values;
   storing, via the control system, the respective compliant value in a database;
   controlling, via the control system, the MR scanner to execute an MR scan in accordance with the MR scan protocol and to set the expected orientation of the logical coordinate system with respect to the coil coordinate system to a first orientation after the MR scan has been started;
   determining, via the control system, a first value for the predefined MR timing parameter according to the first orientation based on data stored in the database; and
   controlling, via the control system, the MR scanner to execute a scan sequence according to the first orientation and the first value.

2. The method according to claim 1, further comprising:
   controlling, via the control system, the MR scanner to execute the MR scan protocol starting with an initial scan sequence according to an initial orientation.

3. The method according to claim 2, wherein the plurality of expected orientations is determined as a sequence of orientations starting with the initial orientation, and
   wherein the compliant value for each of the plurality of expected orientations is determined according to the sequence of orientations.

4. The method according to claim 3, wherein the sequence of orientations is determined such that an orientation angle is incrementally changed by a predefined angular increment starting from an initial angle according to the initial orientation.

5. The method according to claim 3, wherein the sequence of orientations is determined according to a predefined probability distribution associated with the plurality of expected orientations.

6. The method according to claim 1, further comprising:
   receiving, via the control system, a user input associated with the plurality of expected orientations; and
   determining the sequence of orientations according the user input.

7. The method according to claim 1, further comprising:
   determining, via the control system, a closest orientation to the first orientation from among the plurality of expected orientations; and
   determining, via the control system, the first value by reading, from the database, the compliant value corresponding to the closest orientation.

8. The method according to claim 1, wherein the act of determining the first value comprises:
   interpolating respective compliant values identified with two or more of the plurality of expected orientations.

9. The method according to claim 1, further comprising:
   when it is determined that the first orientation deviates from each of the plurality of expected orientations in excess of a predefined tolerance, determining a further compliant value for the MR timing parameter for the first orientation depending on the MR scan protocol and the gradient limit values; and
   storing the further compliant value in the database.

10. The method according to claim 1, further comprising:
    after the MR scan is finished, receiving, via the control system, a further MR scan protocol; and
    when it is determined by the control system that the further MR scan protocol matches the MR scan protocol:
      controlling, via the control system, the MR scanner to execute a further MR scan, and setting the expected orientation of the logical coordinate system with respect to the coil coordinate system to a second orientation after the further MR scan has been started;
      determining, via the control system, a second value for the MR timing parameter according to the second orientation based upon data stored in the database; and
      controlling, via the control system, the MR scanner to execute a further scan sequence according to the second orientation and the second value.

11. The method according to claim 1, further comprising:
receiving, via the control system, a user input comprising the MR scan protocol or a further user input associated with the MR scan protocol.

12. The method according to claim 11, further comprising:
determining, via the control system when the further user input is received, the MR scan protocol based on the further user input.

13. The method according to claim 1, wherein the act of determining the compliant value for one of the plurality of expected orientations comprises:
receiving, via the control system, an initial value for the MR timing parameter;
determining, via the control system, a temporal course of the magnetic field gradient during a hypothetical scan sequence according to the respective one of the plurality of expected orientations;
computing, via the control system, the initial value and the MR scan protocol; and
determining, via the control system, the compliant value for the respective one of the plurality of expected orientations as the initial value only when the computed temporal course of the magnetic field gradient complies with the gradient limit values.

14. The method according to claim 13, further comprising:
when the temporal course of the magnetic field gradient violates the gradient limit values:
adapting, via the control system, the initial value; and
re-computing, via the control system, the temporal course of the magnetic field gradient according to the adapted initial value; and
determining, via the control system, the compliant value for the respective one of the plurality of expected orientations as the adapted initial value only when the re-computed temporal course of the magnetic field gradient complies with the gradient limit values.

15. The method according to claim 1, wherein the act of determining the compliant value for one of the plurality of expected orientations comprises:
executing, via the control system, an optimization of the MR timing parameter,
wherein the MR scan protocol, the respective one of the plurality of expected orientations, and the gradient limit values are treated as boundary conditions.

16. The method according to claim 1, wherein the MR timing parameter comprises one or more of (i), an echo time, (ii) a repetition time, and/or (iii) a frame duration.

17. A magnetic resonance imaging (MRI) system, comprising:
an MR scanner comprising gradient coils configured to generate respective components of a magnetic field gradient along respective coordinate axes of a coil coordinate system; and
a control system configured to:
receive (i) predefined gradient limit values identified with components of the magnetic field gradients in the coil coordinate system, and (ii) a MR scan protocol;
determine a plurality of expected orientations of a logical coordinate system with respect to the coil coordinate system;
determine, for each of the plurality of expected orientations, a compliant value for a predefined MR timing parameter based upon the MR scan protocol and the predefined gradient limit values;
store the compliant value in a database;
control the MR scanner to execute an MR scan in accordance with the MR scan protocol;
set the orientation of the logical coordinate system with respect to the coil coordinate system to a first orientation after the MR scan has been started;
determine a first value for the predefined MR timing parameter according to the first orientation based on data stored in the database; and
control the MR scanner to execute a scan sequence according to the first orientation and the first value.

18. A non-transitory computer readable medium having instructions stored thereon that, when executed by a control system identified with a magnetic resonance imaging (MRI) system comprising gradient coils configured to generate respective components of a magnetic field gradient along respective coordinate axes of a coil coordinate system, cause the MRI system to:
receive (i) predefined gradient limit values identified with components of the magnetic field gradients in the coil coordinate system, and (ii) a MR scan protocol;
determine a plurality of expected orientations of a logical coordinate system with respect to the coil coordinate system;
determine, for each of the plurality of expected orientations, a compliant value for a predefined MR timing parameter based upon the MR scan protocol and the predefined gradient limit values;
store the compliant value in a database;
control the MR scanner to execute an MR scan in accordance with the MR scan protocol;
determine that the orientation of the logical coordinate system with respect to the coil coordinate system is set to a first orientation after the MR scan has been started;
determine a first value for the predefined MR timing parameter according to the first orientation based on data stored in the database; and
control the MR scanner to execute a scan sequence according to the first orientation and the first value.

* * * * *